United States Patent [19]
Milijasevic et al.

[11] Patent Number: 5,499,968
[45] Date of Patent: Mar. 19, 1996

[54] FLOW CONTROLLERS FOR FLUID INFUSION SETS

[75] Inventors: Zoran Milijasevic; Graham Bode, both of Turrella, Australia

[73] Assignee: Macnaught Pty Limited, Turrella, Australia

[21] Appl. No.: 272,232

[22] Filed: Jul. 8, 1994

Related U.S. Application Data

[62] Division of Ser. No. 923,927, Oct. 21, 1992, Pat. No. 5,356,376.

[30] Foreign Application Priority Data

Mar. 8, 1990 [AU] Australia .................................. P J 9008

[51] Int. Cl.⁶ ...................................................... A61M 1/00
[52] U.S. Cl. .............................. 604/30; 604/252; 604/246
[58] Field of Search ................................... 604/30, 84.87, 604/246, 251, 252, 248, 81, 122

[56] References Cited

U.S. PATENT DOCUMENTS

| | | |
|---|---|---|
| 772,279 | 10/1904 | Grouvelle et al. . |
| 1,850,030 | 3/1932 | Pardoe . |
| 2,044,806 | 6/1936 | Naiman . |
| 2,127,501 | 8/1938 | Dall . |
| 2,770,234 | 11/1956 | Nesset et al. . |
| 2,790,463 | 4/1957 | Delano et al. . |
| 2,842,962 | 7/1958 | Dall . |
| 2,868,013 | 1/1959 | Terrell . |
| 2,952,253 | 9/1960 | Seligman et al. . |
| 2,979,067 | 4/1961 | Kern, Jr. et al. . |
| 3,109,459 | 11/1963 | Lee II et al. . |
| 3,111,091 | 11/1963 | Hopkinson . |
| 3,156,225 | 11/1964 | Linn . |
| 3,282,768 | 11/1966 | Caines et al. . |
| 3,298,367 | 1/1967 | Bergman . |
| 3,469,745 | 9/1969 | Serio, Jr. et al. . |
| 3,489,172 | 1/1970 | Whitmore . |
| 3,504,663 | 4/1970 | Edwards . |
| 3,517,700 | 6/1970 | Williams et al. . |
| 3,620,500 | 11/1971 | Santomieri . |
| 3,628,140 | 12/1971 | Hogg et al. . |
| 3,642,030 | 2/1972 | Amick . |
| 3,702,144 | 11/1972 | Loveland . |
| 3,841,270 | 10/1974 | Sokolowski . |
| 3,868,973 | 3/1975 | Bierman et al. . |
| 3,877,248 | 4/1975 | Honnold, Jr. . |
| 3,893,451 | 7/1975 | Durand et al. . |
| 3,894,562 | 7/1975 | Moseley, Jr. et al. . |
| 3,999,714 | 12/1976 | Lang . |
| 4,105,721 | 8/1978 | Schliebe . |

(List continued on next page.)

FOREIGN PATENT DOCUMENTS

| | | |
|---|---|---|
| 32068/68 | 7/1969 | Australia . |
| 89974/82 | 6/1983 | Australia . |
| 89304/82 | 9/1983 | Australia . |
| 30035/84 | 4/1985 | Australia . |
| 38861/89 | 7/1989 | Australia . |
| 629228 | 2/1993 | Australia . |
| 1259805 | 1/1972 | United Kingdom . |
| WO85/04460 | 10/1985 | WIPO . |

OTHER PUBLICATIONS

Abstract of Australian application AU-A-38861/89, filed Jul. 21, 1989, published Jan. 25, 1990.

*Primary Examiner*—John D. Yasko
*Attorney, Agent, or Firm*—Fisher, Christen & Sabol

[57] ABSTRACT

An in-line fluid flow controller for use with a fluid administration set for infusion of fluid into the body of a patient, the administration set comprising a reservoir of fluid connected to a supply line having a discharge orifice; characterized in that the fluid flow controller comprises a housing having a chamber therein, an inlet to and an outlet from said chamber, said housing being adapted to receive therewithin at least one flow restrictor each having an orifice or orifices configured to control the rate of fluid flow therethrough and into the body of a patient such that the fluid is infused into a patient at a predetermined constant flow rate or at a flow rate within predetermined limits via said discharge orifice.

27 Claims, 12 Drawing Sheets

U.S. PATENT DOCUMENTS

| | | |
|---|---|---|
| 4,143,853 | 3/1979 | Abramson . |
| 4,324,112 | 4/1982 | Fujiwara et al. . |
| 4,338,969 | 7/1982 | Usry . |
| 4,343,305 | 8/1982 | Bron . |
| 4,395,260 | 7/1983 | Todd et al. .......................... 604/252 X |
| 4,396,016 | 8/1983 | Becker ................................ 604/252 X |
| 4,484,472 | 11/1984 | Licinit et al. . |
| 4,688,755 | 8/1987 | Pluviose . |
| 4,695,272 | 9/1987 | Berglund et al. ........................ 604/84 |
| 4,781,698 | 11/1988 | Parren ..................................... 604/246 |
| 4,807,660 | 2/1989 | Asianian . |
| 4,822,344 | 4/1989 | O'Boyle . |
| 5,014,750 | 5/1991 | Winchell et al. . |

FIG. 6A
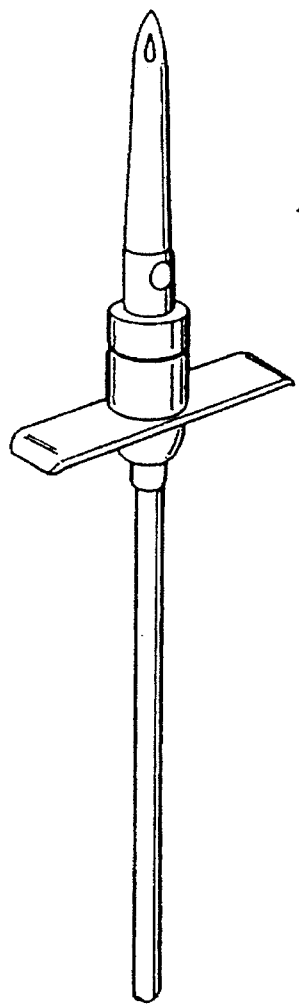
FIG. 6B
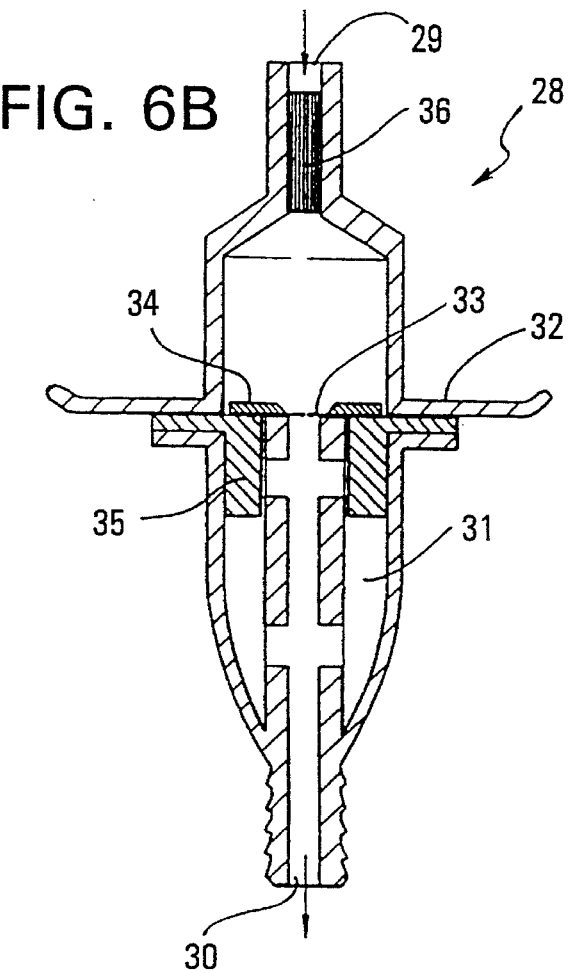
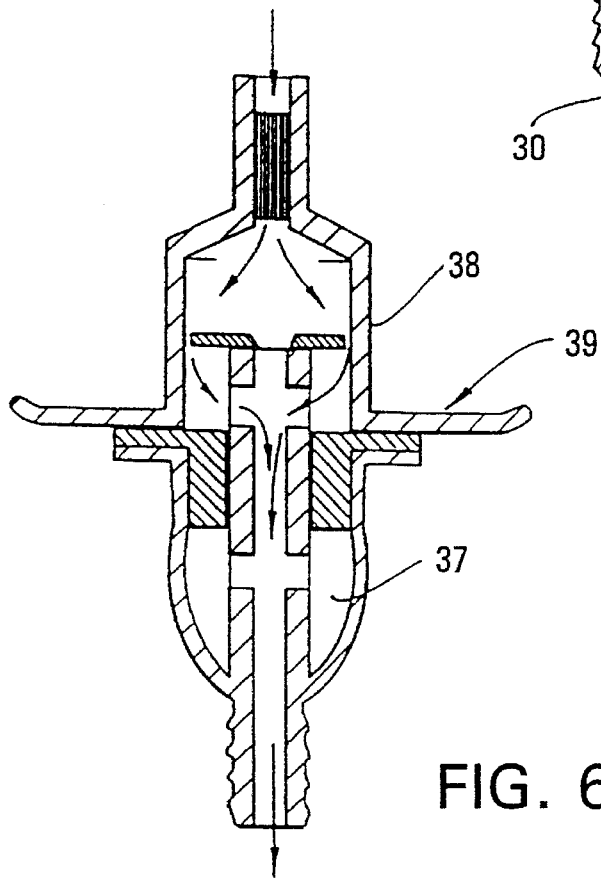
FIG. 6C

FLOW CONTROLLERS FOR FLUID INFUSION SETS

This is a divisional of application Ser. No. 07/923,927, now U.S. Pat. No. 5,356,376 filed on Oct. 21, 1992, which is a 371 of PCT/AU91/00083, filed Mar. 4,1991.

FIELD OF THE INVENTION

The present invention relates to flow controllers for administration sets for the purpose of delivering fluids into the human body. Infusing fluids into the human body is done for a variety of medical reasons and there have been many administration sets which have been developed for this purpose.

BACKGROUND OF THE INVENTION

It is presently well known to provide for liquid infusion into a living body by providing a container, acting as a reservoir for holding liquid to be infused and which is connected to the body via a conduit in which pressure supplying the fluid is created by either a gravitational pressure head or by pressure generation means.

In these systems there are three main factors controlling the actual infusion rate of the liquid to be infused into a patient. The first is the height that the liquid container is held relative to the outlet and the second factor is the degree of back pressure which is experienced as the liquid enters the patient. It is a disadvantage in such a simple arrangement that the back pressure can provide significant changes in flow rate and this can be altered almost casually without intention by the patient perhaps rolling over in bed or simply changing to a more comfortable position. A third factor is the viscosity of the fluid being infused. The viscosity can be changed due to temperature variation or change of fluid. As fluids have different viscosities fluid flow rate changes of up to 8% can be caused by this difference alone.

Furthermore, it is necessary on many occasions to keep the flow rate of the liquid within selected limits and this becomes either very difficult or impossible with the simple gravitationally actuated device of the type discussed.

Thus, in the past it has been very difficult to provide a fluid for infusion into a body at a constant flow rate and to ensure that a selected quantity of the fluid is infused into the body at any given time and with a high degree of accuracy and without the unwanted effects of back pressure. The present invention seeks to improve administration sets used for the purpose of infusing fluids into the human body by providing a flow controller which is adapted to be used as an attachment to the administration set or alternatively to be integral with an administration set.

SUMMARY OF THE INVENTION

The present invention therefore comprises: a fluid flow controller for insertion in a selected position in a fluid flow line of an administration set. More particularly, the invention resides in a flow controller adapted for detachable or fixed attachment to an administration set, said flow controller essentially comprising; a housing having a chamber inside which a flow restrictor fits and which is adapted to enable attachment to the administration set or to be integral therewith, wherein when fluid flows through said administration set to a patient via said flow controller said flow restrictor thereby restricts the flow of fluid to the extent that the fluid discharged into the body of said patient takes place at a relatively constant rate largely irrespective of viscosity or fluid or body temperature.

The present invention seeks to provide a convenient form of providing a controlled flow in an administration set and like infusion apparatuses and to overcome the aforementioned problems.

In embodiments of the present invention the fluid flow controller comprises;
a housing having a chamber therein, an inlet to and outlet from said chamber, said housing being adapted to receive therewithin at least one restrictor having an orifice or orifices configured to control the rate of fluid flow therethrough and into the body of a patient such that the fluid is infused into a patient at a predetermined constant flow rate at a flow rate within predetermined limits via said discharge orifice. In an alternative form, the present invention comprises:
a fluid flow controller for inclusion in a fluid flow line of an administration set for infusing fluids into the body of a patient, said fluid flow controller comprising a housing adapted to accommodate therein at least one restrictor, said housing comprising an inlet and an outlet which are associated with a priming chamber.

In the preferred embodiment, the flow controller comprises a resiliently deformable housing which facilitates evacuation of the supply line or transmission of a fluid there along to prime the supply line either upstream or downstream of said at least one restrictor.

In a further embodiment the fluid flow controller is adapted for detachable attachment to the fluid supply line of an administration set or alternatively, fabricated integral with the fluid supply line of an administration set.

BRIEF DESCRIPTION OF THE DRAWINGS

The present invention will now be described in more detail and with reference to preferred but non limiting embodiments wherein:

FIGS. 6a, 6b and 6c show views of another embodiment of a flow controller adapted for insertion in a fluid supply line of an administration set as shown in FIG. 1.

DETAIL DESCRIPTION OF THE INVENTION

Figure 1:
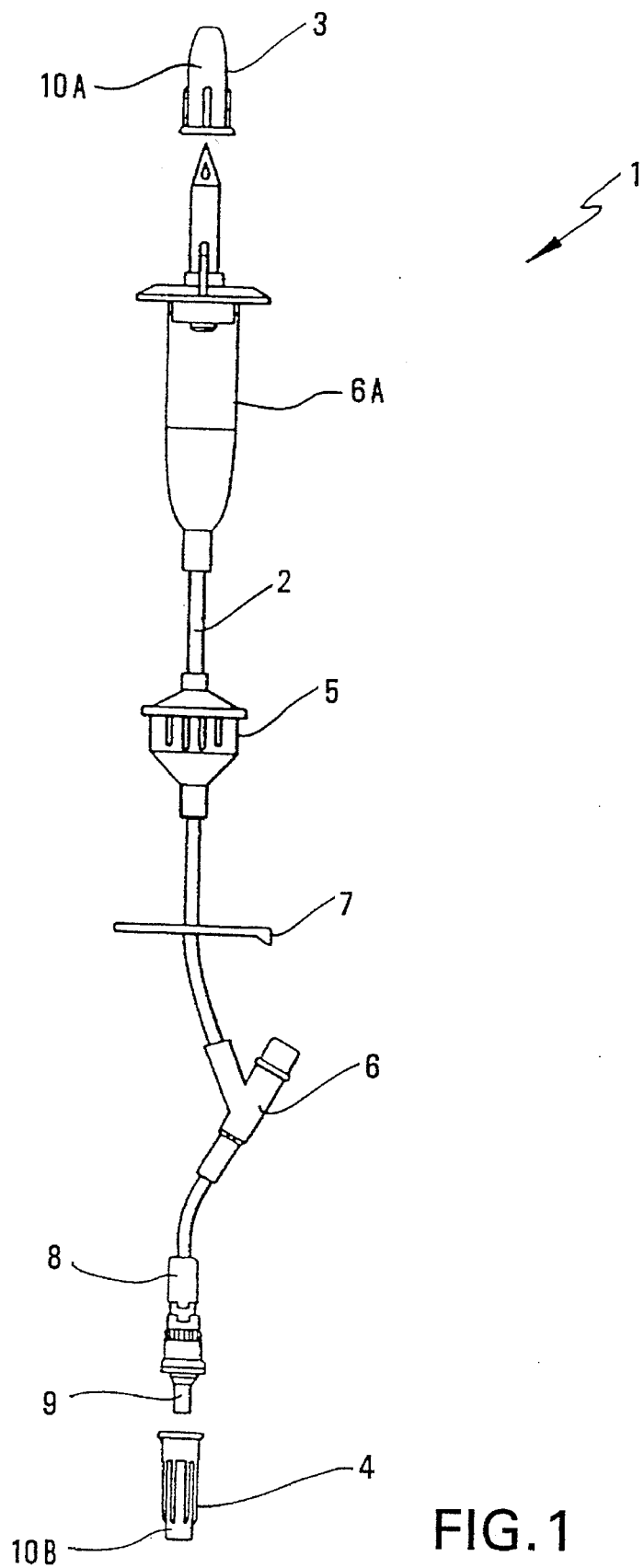
FIG. 1: shows a schematic layout of a typical administration set with the fluid flow controller inserted in a preselected position in the fluid supply line.

Referring to FIG. 1 there is shown an administration set 1 comprising a fluid supply line 2 which runs between a fluid reservoir end 3 and a fluid discharge end 4.

Intermediate the said reservoir end 3 and end 4 is a flow controller 5 which may be inserted in the fluid supply line as an attachment to the administration set 1 or alternatively, as an item integral with the supply line 2.

In addition, the fluid supply line 2 is adapted with a dip chamber 6A an injection port, a plastics slide clamp 7, a flash ball 8, a luer connector 9 and tip protectors 10A and 10B to form one possible configuration of administration set.

Although the embodiment shown has a number of features in the fluid supply line, in its simpliest form, an administration set may simply have a reservoir, a fluid flow line and a flow controller upstream of an outlet.

Figure 2:
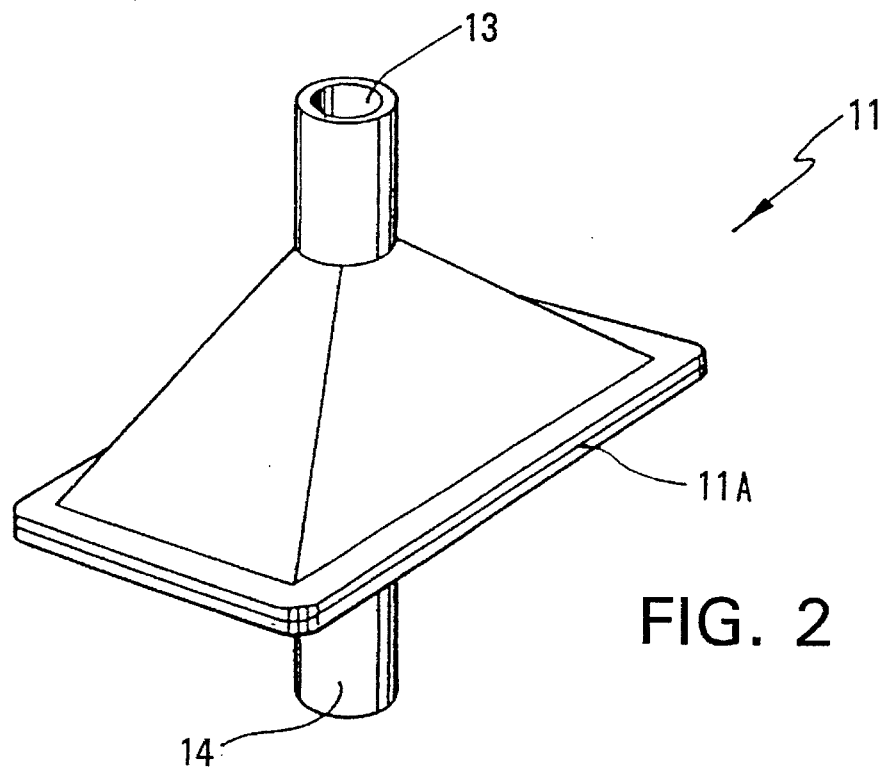
FIG. 2: shows an isometric view of one preferred embodiment of the flow controller adapted for detachable attachment to the fluid supply line.

FIG. 2 shows the flow controller according to one preferred embodiment of the invention. The flow controller 11 in FIG. 2 comprises a housing 11A, which is adapted to house a restrictor 12 (see FIG. 3), an inlet and an outlet 14.

Preferably the housing 11A is comprised of a resiliently deformable but elastic material which enables the priming of the fluid flow line or urging of fluid along said flow line for releasing air from the flow line.

Figure 3:
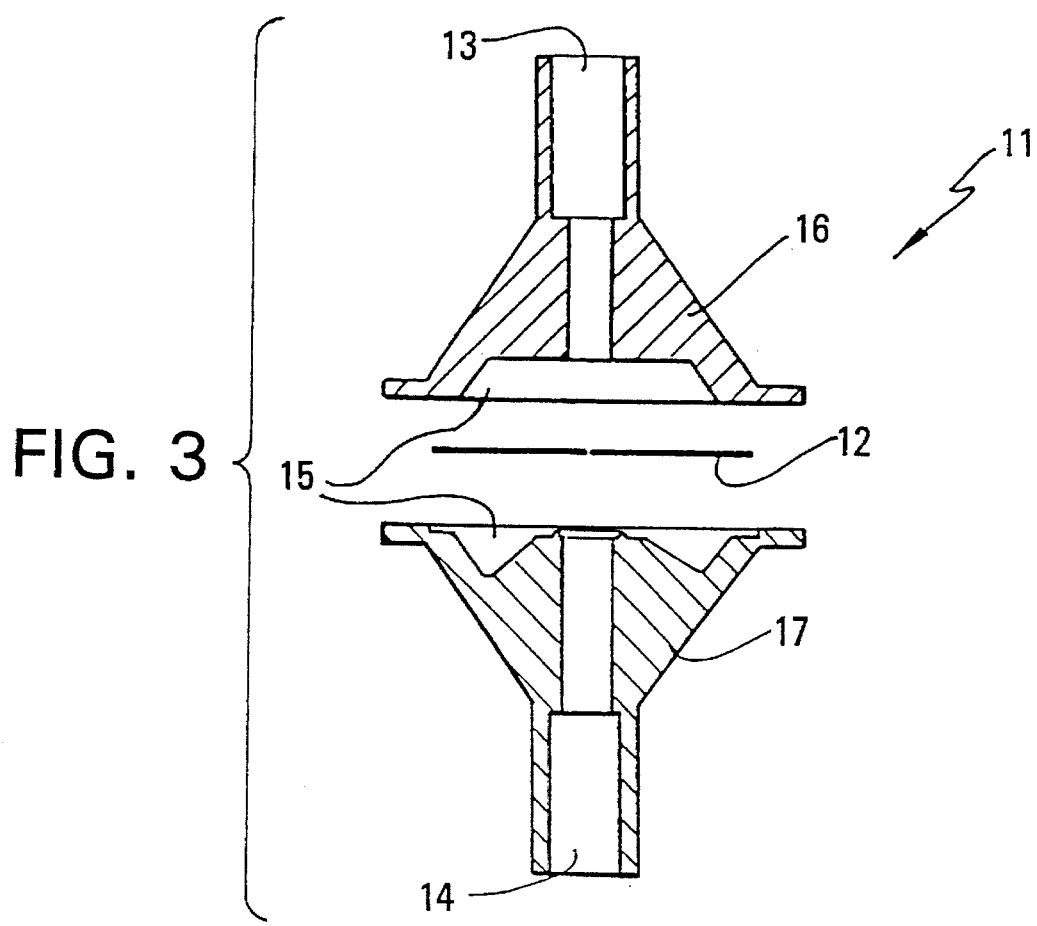
FIG. 3: shows an exploded side view of the flow controller shown in FIG. 2.

FIG. 3 shows the flow controller of FIG. 2 in a cross sectional exploded view. From FIG. 3 it can be seen that the housing 11A is comprised of components 16 and 17. These are separable and provide a means for enabling insertion of the restrictor 12 therein. When components 16 and 17 are joined, a priming chamber 15 is formed. As can be seen from FIG. 3, the inlet and outlet 13 and 14 are in alignment with each other and also in axial alignment with the priming chamber 15. The restrictor in this embodiment is shown as a single plate with a single orifice.

Figure 4:
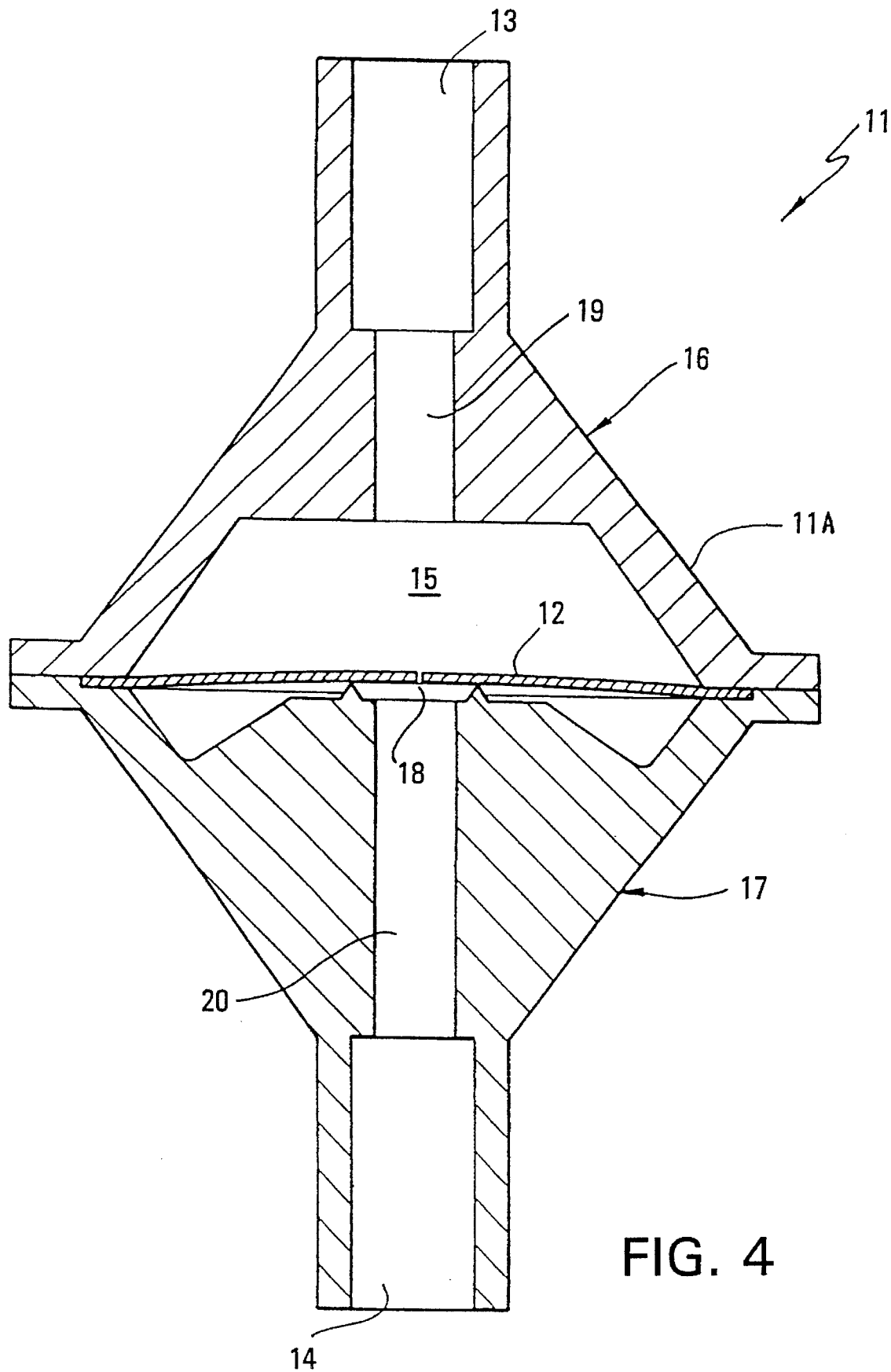
FIG. 4: shows an enlarged cross-sectional view of the flow controller of FIG. 2 showing the restrictor plate spanning the flow chamber.

FIG. 4 shows an assembled view of the flow controller with the components 16 and 17 of the housing 11A. In doing this they secure the restrictor or orifice plate 12 such that a barrier is presented substantially normally to the axis of the fluid flow line which is in turn axially aligned to ends 13 and 14 of the housing 11A. The orifice is adapted with a geometrically designed hole 18 which can be seen in FIG. 4 and this has been made the subject of applicants' co-pending U.S. application Ser. No. 480,290, filed Apr. 16, 1990, which has been abandoned in favor of co-pending continuation-in-part application Ser. No. 875,765, filed Apr. 29, 1992.

In this configuration with the flow controller attached to the fluid supply line, the housing 11A receives fluid via inlet 13 axially along the passage 19 and into the chamber 15. The geometry of the hole 18 enables the fluid to be delivered at a constant flow along passage 20 and via outlet 14 and distal part of the administration set into the body of a patient. The housing 11A can either be detachably affixed to the fluid supply line or moulded integral with the fluid supply line such that the inlet 13 is to be regarded as of indefinite length; so to the outlet 14. It should be noted that the shape and configuration of the housing as illustrated in FIGS. 2 to 4 shows merely one embodiment of many different embodiments of a detachable or fixedly attached fluid flow controller for use with an administration set in a fluid supply line.

Figure 5:
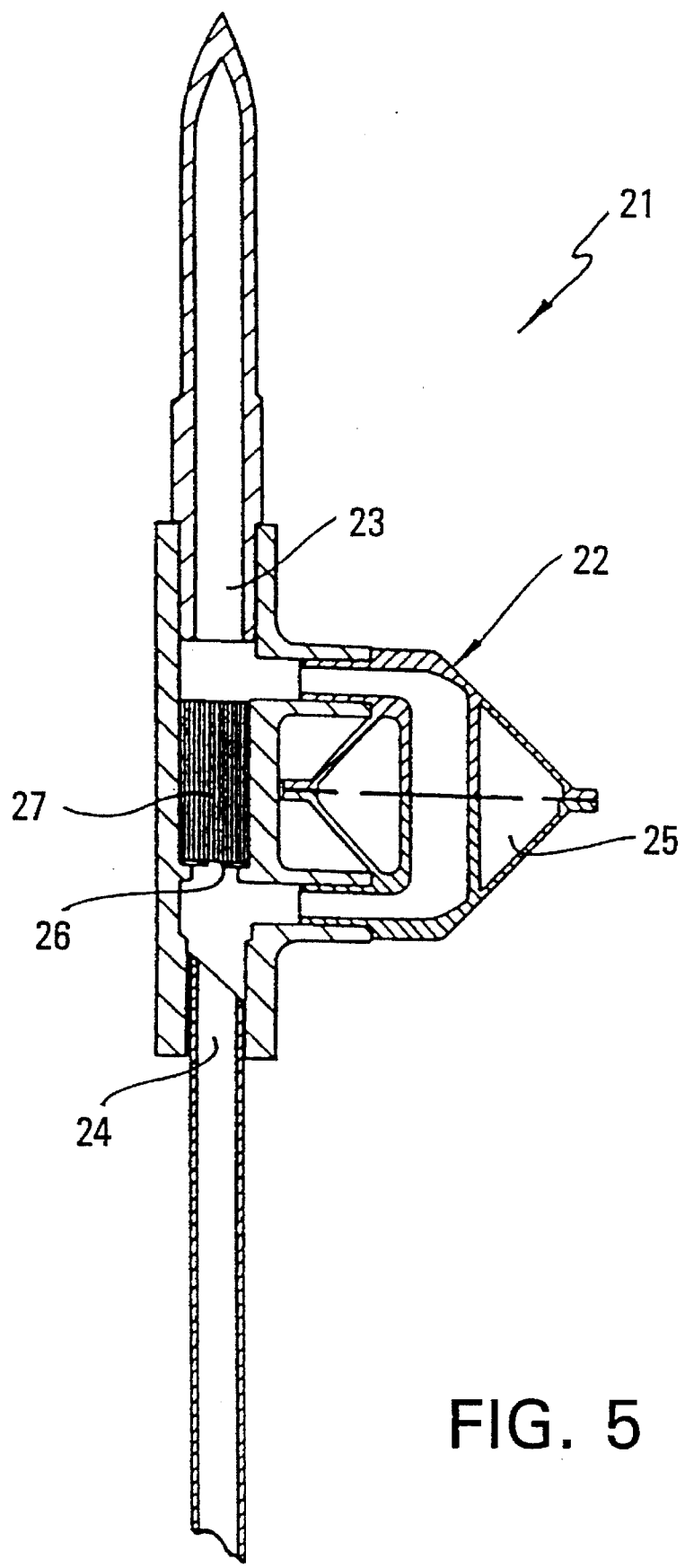
FIG. 5: shows a flow controller according to an alternative embodiment wherein the flow chamber is eccentric to the axial alignment of the inlet and outlet to the flow controller.

Referring to FIG. 5 there is shown a further embodiment of a flow controller 21. This particular embodiment of flow controller also adapted for detachable or fixed attachment to an administration set supply line comprises a housing 22 comprising an inlet 23 an outlet 24 and a priming chamber 25. The housing 22 also comprises means to enable the adapt ion of a restrictor plate 26 and also the insertion of a hydrophilic filter 27 therein for the purpose of filtering the fluids which flow therethrough. It is to be noted that in this embodiment the priming chamber is parallel to the inlet 23 and outlet 24.

FIGS. 6a and 6b show a further embodiment of a flow controller 28 having an axially aligned inlet and outlet 29 and 30 respectively, in addition to a priming chamber 31 to form a flow controller housing 32. The housing 32 is adapted to receive a restrictor plate 33 for insertion in such a way that it is used in conjunction with a top seal 34 and a side seal 35. In this embodiment the housing 32 is also adapted with a hydrophilic filter 36 at the inlet 29 for the purpose of filtering the fluid which flows therethrough prior to passing through the this time with a shortened priming chamber 37 and a reconfiguration of the sealing and restriction in the upper portion 38 of the housing 39.

Figure 7:
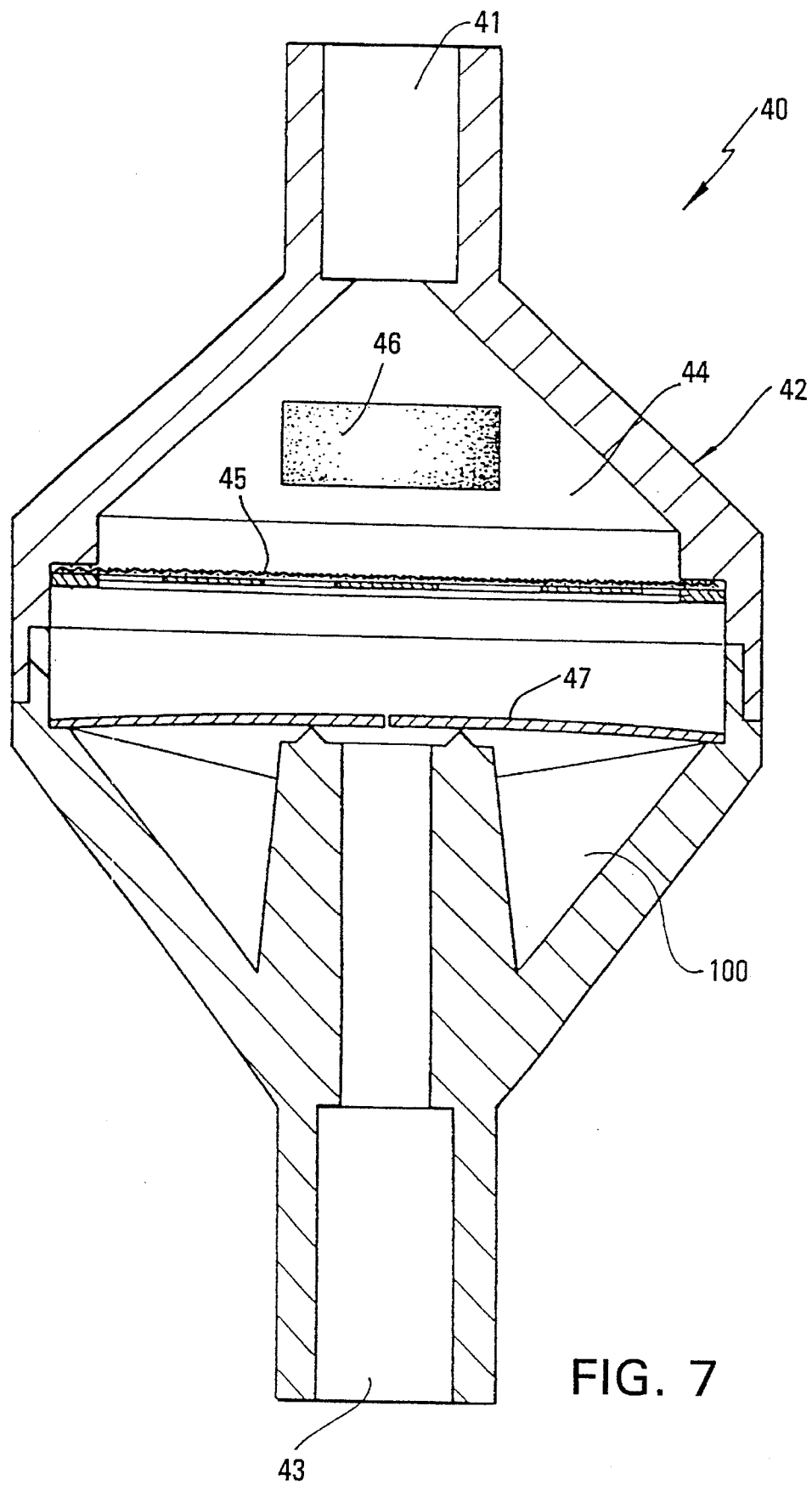
FIG. 7: shows an elevational view of a longitudinal cross-section of a flow controller with a filter according to a preferred embodiment of the present invention.

FIG. 7 shows an alternative embodiment of the flow controller 40 showing an inlet passage 41 entering a housing 42 also connected to an exit passage 43. The housing 42 has therein a chamber 44, having located therein a hydrophilic filter 45, a hydrophobic filter 46 and an orifice plate 47. The hydrophobic filter 46 comprises a hydrophobic mesh material which allows air to escape to the atmosphere but prevents the fluid from exiting.

In order to prime the flow controller 40 in FIG. 7, pressure is exerted in a direction lateral to the axial direction of the inlet and outlet tubes. The consequent is that it allows the fluid to bypass the orifice plate and to prime the flow controller prior to use.

The orifice plate stays relatively still and the sealing spigot moves away from the plate when the controller is squeezed. This occurs with the assistance of webs 100.

The above described embodiments are examples of a number of different embodiments which can be used in the present application in order to achieve a constant flow rate in a given administration set.

The critical features of the present invention reside in the existence Of a housing having an inlet and an outlet with a chamber therein being adapted to accommodate at least one restrictor for the purpose of delivering via the outlet a constant flow rate of infusing fluid. In attaching the fluid flow controller to the administration set, it is envisaged that the connection can be done in any one of the number of different ways including conventional means for fitting tubing together. This would include sleeve fitting, flange mating, slot fitting, clamp fitting.

In an alternative embodiment of the present invention, it is envisaged that the administration .set may be adapted so as to deliver a predetermined liquid flow rate via a series of flow controllers linked either in series or in parallel. It is also to be understood that the present invention is not to be restricted to the delivery of fluids for administration into the human body but can also be used for delivery of fluids in a variety of different applications where fluid is to be delivered at a constant flow rate independent of temperature.

It will be appreciated that the present invention as broadly described herein can be varied somewhat to include a variety of different embodiments including alteration of the location of each flow controller along the supply line of an administration set, altering the configuration of the housing, altering the configuration of the chamber within which the restrictor fits, altering the relative position of the restrictor in relation to the outlet and inlet of the flow control housing and providing the flow control housing as a one piece or multiple piece unit either pre-assembled or adapted for assembly at site.

Ideally, each flow control chamber would be adapted with a hydrophilic filter in order to remove particulate matter large enough to block the orifice.

In one embodiment of the present invention the invention comprises an administration set with the flow controller adapted integrally therewith. In this type of embodiment and indeed in the embodiment whereby the flow controller can be detachably affixed to the fluid supply line of an administration set the fluid supply line can also be adapted with a valve which enables by-pass of fluid or release of air from the fluid supply line for the purpose of priming prior to use.

Figure 8:
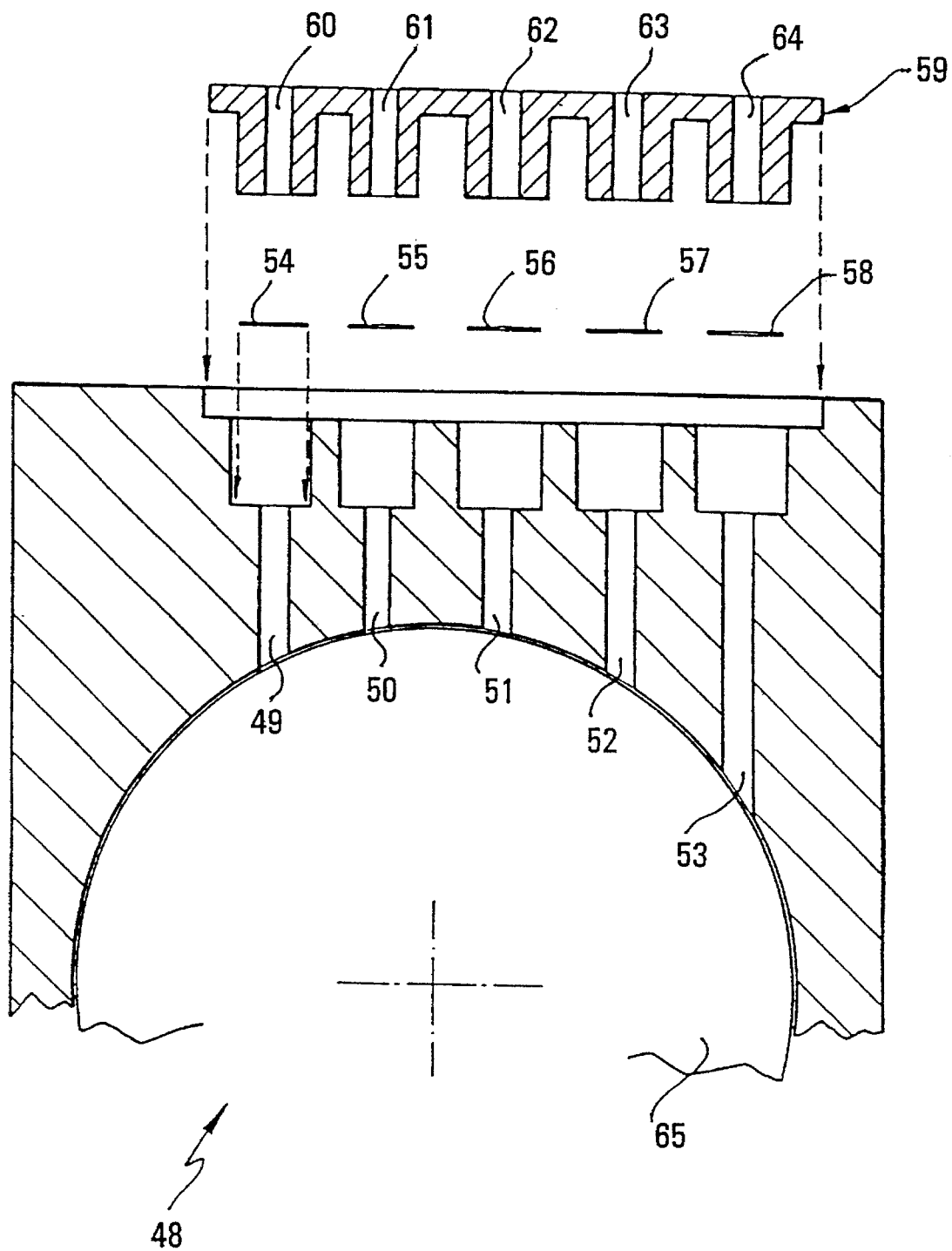
FIG. 8: shows a long sectional view of a multiple flow controller with multiple restrictor plates each with one orifice.

FIG. 8 shows a long sectional view of a multi-flow controller 48 according to an alternative embodiment of the invention.

Figure 9:
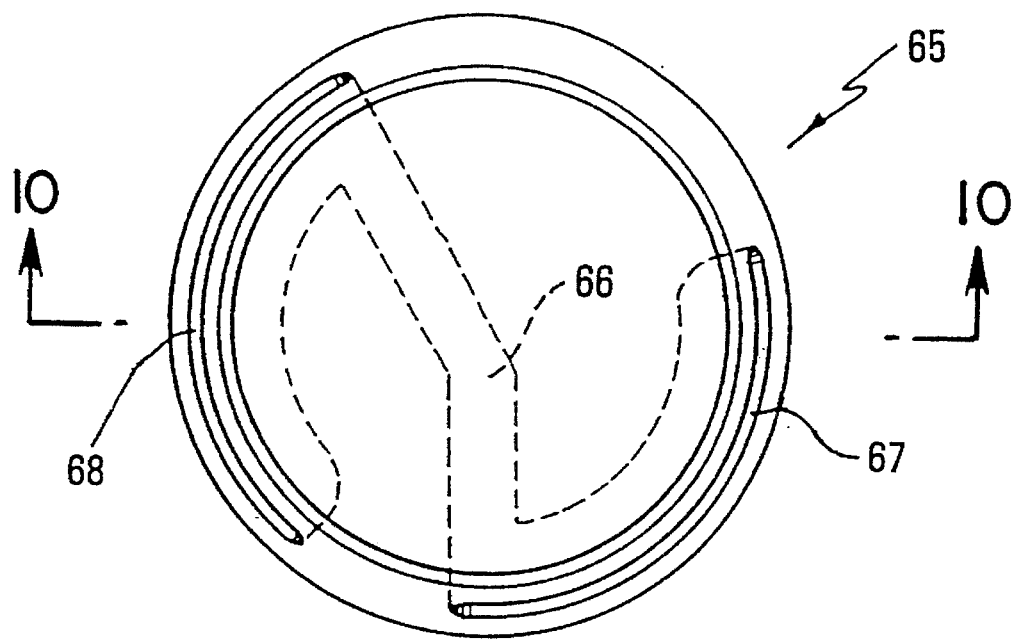
FIG. 9: shows a plan view of a rotatable member of a flow controller according to a preferred embodiment with passages adapted to align with the channels leading to each circular restrictor plate of FIG. 8.
Figure 10:
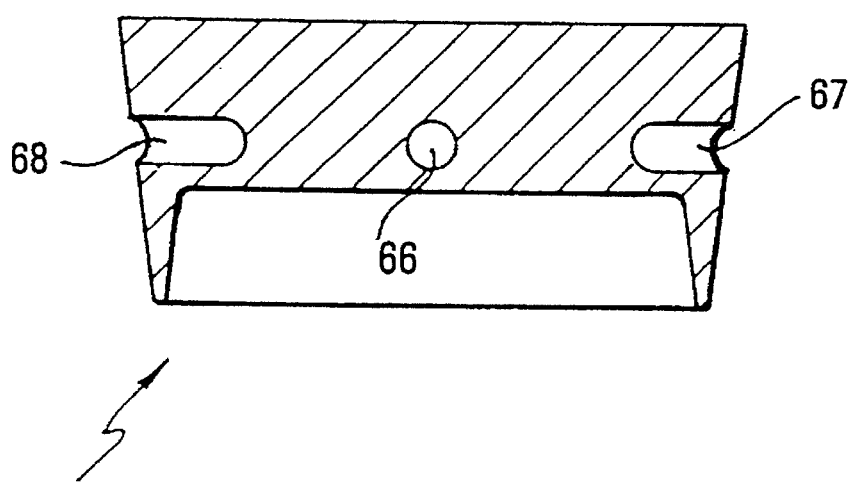
FIG. 10 shows a cross section through the member of FIG. 9.

The controller 48 as shown in FIG. 8 is adapted with a series of passages 49, 50, 51, 52 and 53. The passages are linked with a series of orifice plates 54, 55, 56, 57 and 58 respectively. The orifice plates are held in position by means of wedge 59 which is adapted with a series of passages 60, 61, 62, 63 and 64 which are aligned with holes in the orifice plates and with the corresponding passages 49, 50, 51, 52 and 53. In use, fluid passes through the orifices in the array of restrictor plates 54, 55, 56, 57 and 58 upon selection of a flow rate by rotatable member 65. FIG. 9 shows a side elevational view of the rotatable member 65. This member is adapted to rotate in a clockwise or anti-clockwise direction according to a selected fluid flow requirement. The rotatable member 65 is adapted with a passage 66 and grooves 67 and 68. When fluid flow is to be selected, the rotatable member 65 is rotated according to one selection such that the groove 68, as shown in FIG. 10 presents to passage 49 where a single flow is required. Where a combination of flows are required through more than one restrictor plate, the groove 68 is presented to one of passages 50, 51, 52 or 53. When any one of these passages are selected, fluid then flows through grooves 67 and 68, and depending upon the presentation of the grooves 67 and 68 relative to the passages 49 to 53, fluid will flow through passage 49 and one or more of passages 50 to 53. Using this method a number of different combinations of flows can be achieved depending upon which of passages 49 to 53, groove 68 of the rotatable member 65 is presented to.

Figure 11:
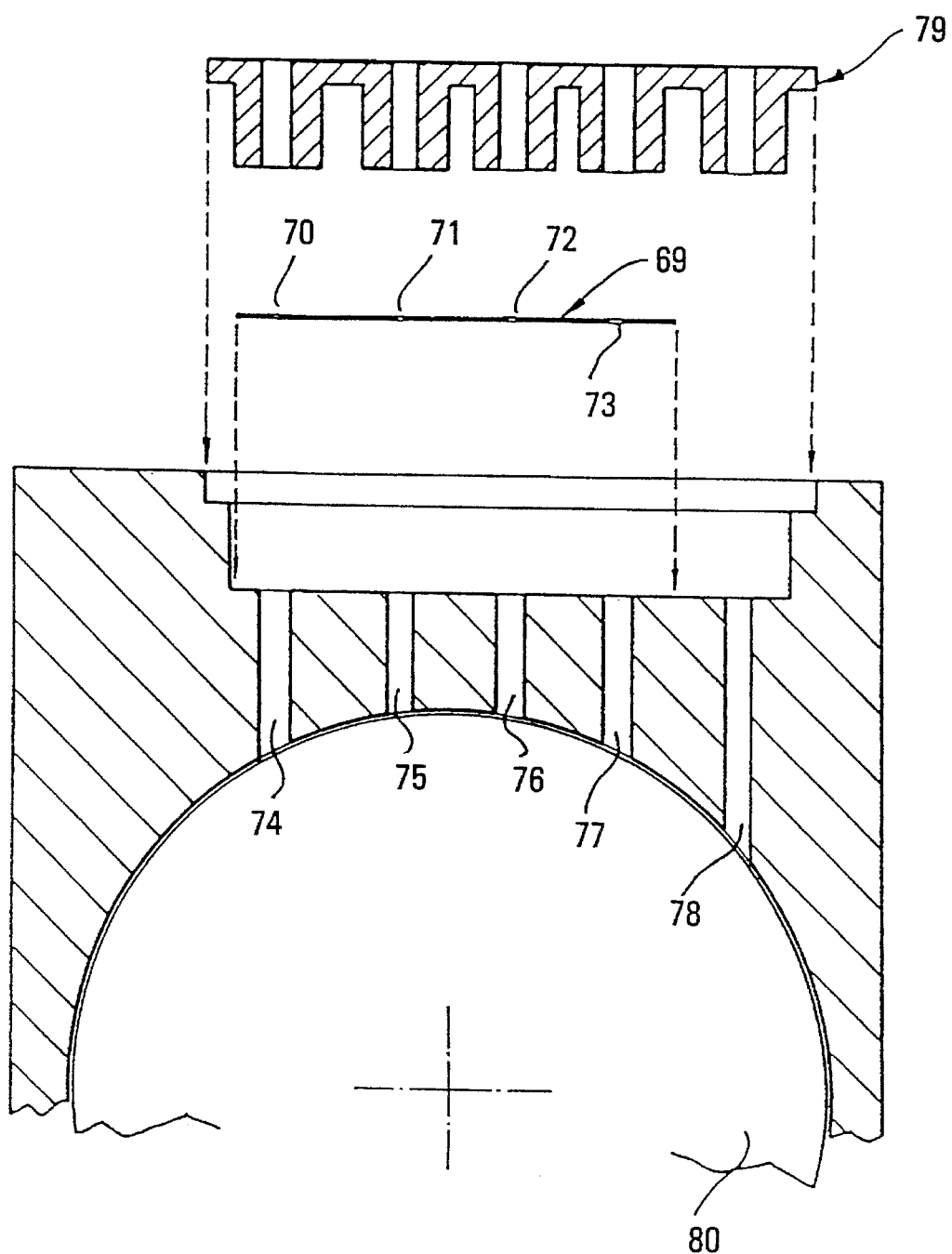
FIG. 11: shows a long sectional view of a multiple flow controller according to one embodiment of the invention having a single plate with multiple orifices.

FIG. 11 shows a similar configuration of an () exploded multiple flow controller this time however a single orifice plate 69 is used with a series of apertures of the same or different diameters. These apertures 70, 71, 72 and 73 are presented to passages 74, 75, 76, and 77. Passage 78 is used for priming purposes or free flow of fluid. Wedge 79 is used to locate the plate in position and also to provide upstream passages for fluid to present to the apertures. In a similar manner to that described for the flow controller of FIG. 8, rotatable member 80 operates by rotation in either an anti clockwise or clockwise direction to select fluid flow. As with the controller of FIG. 8, a single flow or multiple flows can be chosen according to the manner in which the groove (not shown) in rotatable member 80 which corresponds to the groove 68 of rotatable member 65 presents to either one of passages 74, 75, 76, 77 and 78.

Figure 12:
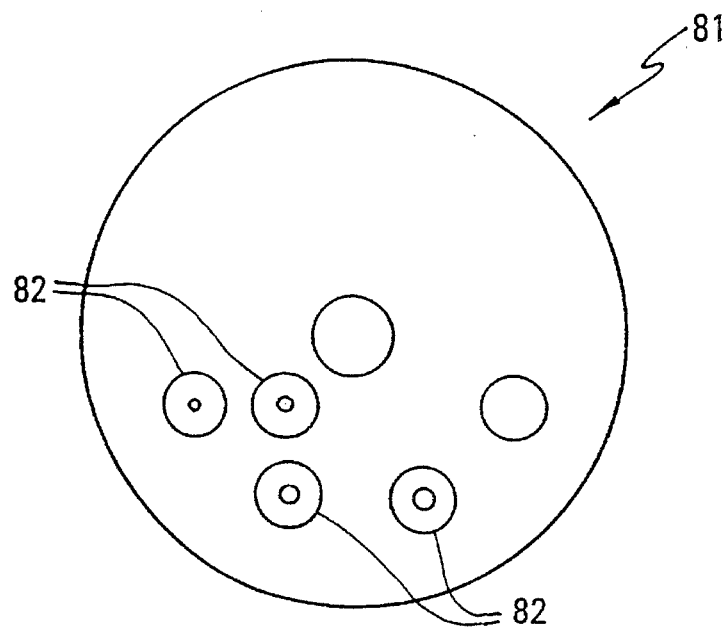
FIG. 12: shows a plan view of a circular restrictor plate with radially disposed orifice plates.
Figure 13:
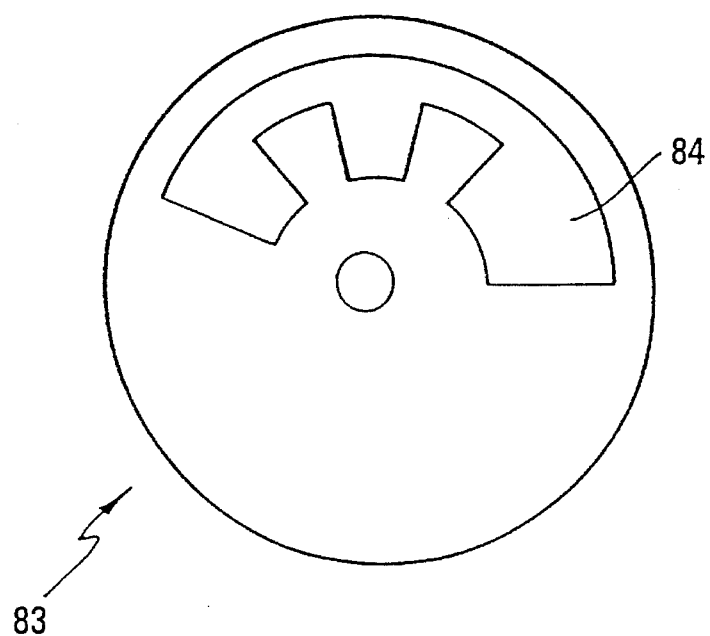
FIG. 13: shows a plan view of drainage passages overlaid by the restrictor plate of FIG. 12.

FIG. 12 shows an alternative embodiment of a restrictor plate housing 81 having radially disposed holes 82, which are located on that plate according to flow requirements. The housing 81 is superimposed over the rotatable drainage facilitator 83 shown in FIG. 13 such that when a flow selection is made, one or more of the orifices 82 present to drainage passage array 84 in the rotatable member 83.

Figure 14:
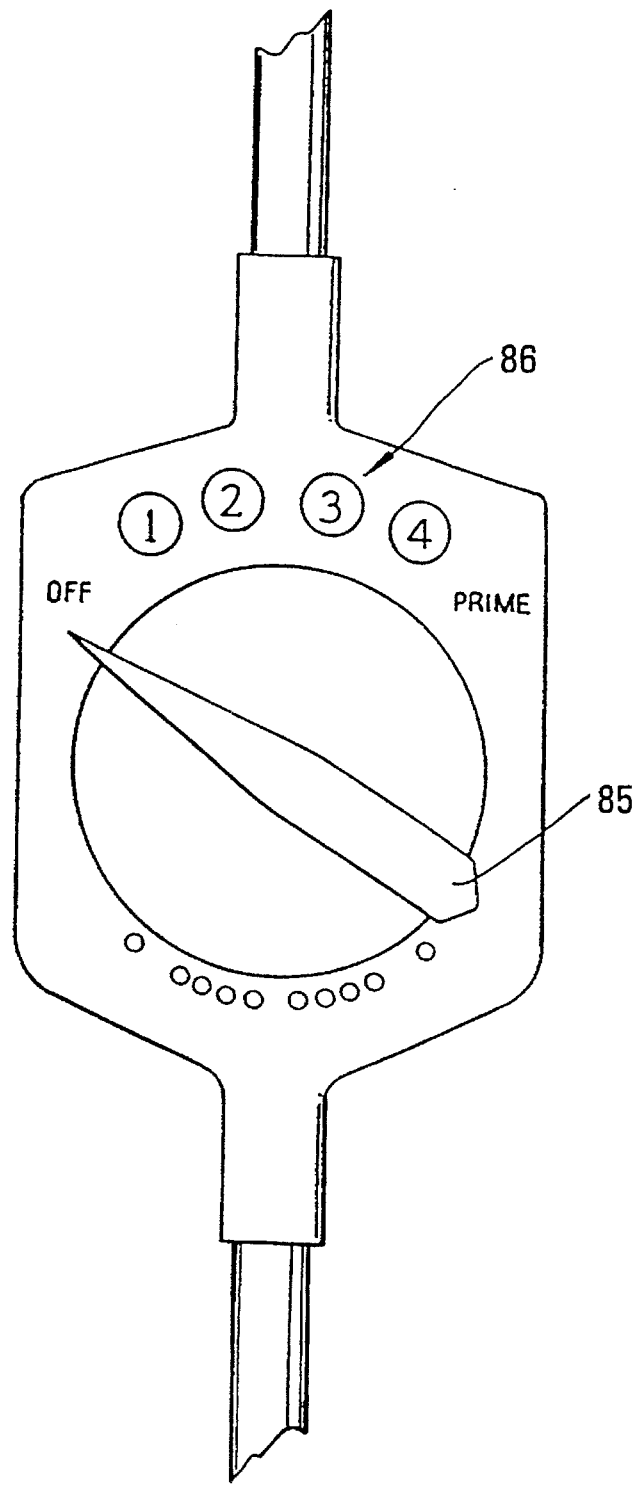
FIG. 14: shows an elevational view of an adjustable multi-flow controller according to one embodiment.
Figure 15:
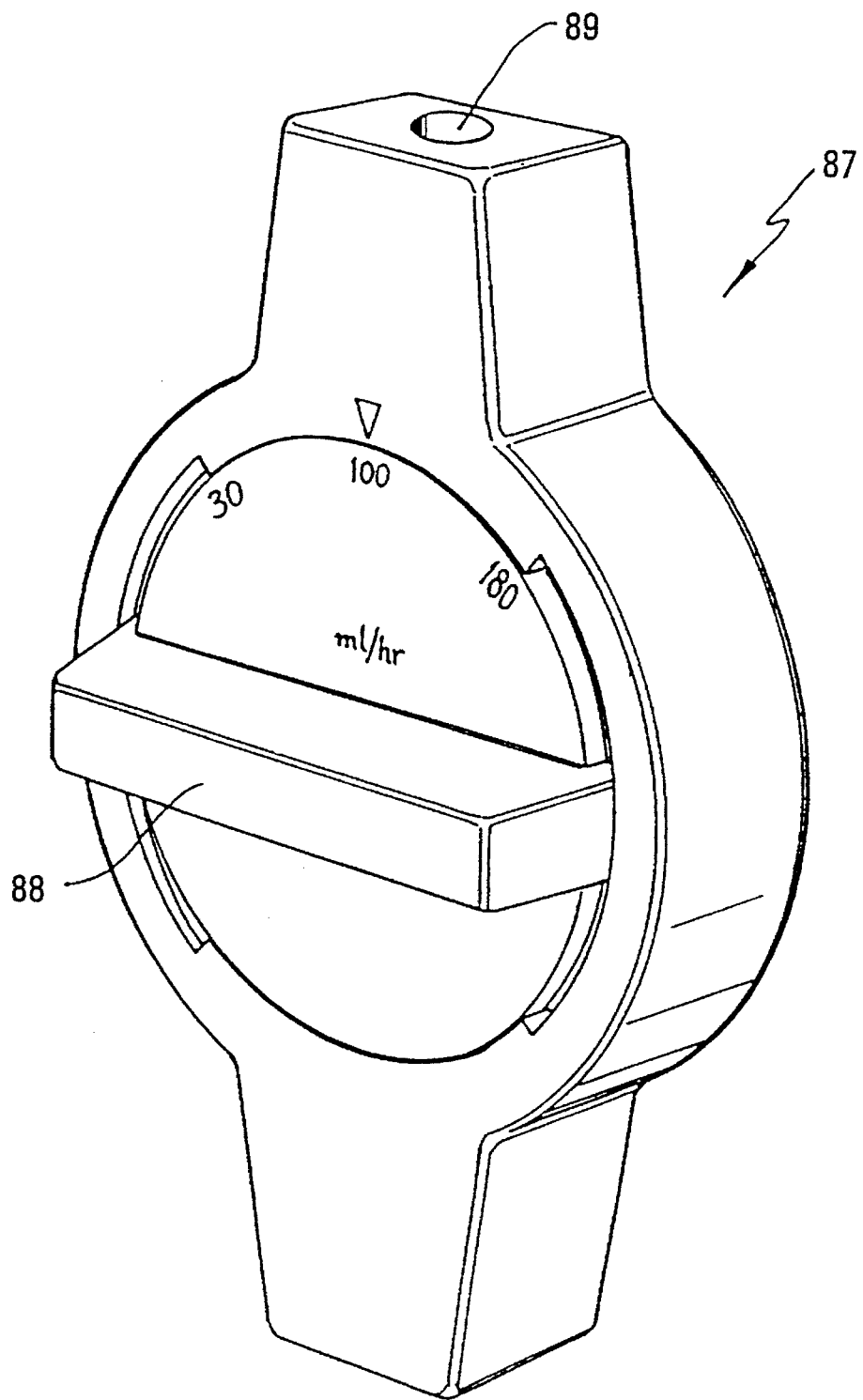
FIG. 15: shows an elevational view of an adjustable multi flow controller according to an alternative embodiment.

FIG. 14 shows an elevational view of the external design of a multi-flow controller showing an external flow selector handle 85 with selection gradations 86. FIG. 15 shows an alternative embodiment of the flow controller 87 having a rotatable flow selector 88. The flow controller 87 has an inlet 89 and an outlet (not shown) which engages with a supply line in a typical administration set.

Ideally flows of 0.5 liters per day, 1 liter per day, 2 liters per day or 3 liters per day are selected either singly or in combination. It will be recognised that the flow characteristic through the orifices in the restrictor plate or plates is dictated by the geometry of the orifice. The subject of the orifice geometry has been made the subject of applicants' co-pending U.S. application Ser. No. 480,290, filed Apr. 16, 1990, which corresponds to Australian Application 38861/89, filed Jul. 21, 1989 which was published on Jan. 25, 1990, and is now Australian Patent No. 629228, sealed Feb. 18, 1993, said U.S. Ser. No. 480,290 being abandoned in favor of co-pending continuation-in-part application Ser. No. 875, 765, filed Apr. 29, 1992.

It will be recognised that it is possible to make a number of different variations to the various embodiments of the present invention described including varying the size of the orifices in the restrictor plates, the spacing between orifices, varying the number of separate restrictor plates and consequently the number of flow through passages, varying the number of combinations of a flow rate selection by varying the number of free passages. The hole sizes of the restrictor plates may fall within the range of 5 microns to 100 microns. Preferably, the orifice sizes of the restrictor plates fall within the range 50 microns to 100 microns. It will also be appreciated that the present invention can be utilised with gravity feed, administration sets or administration sets which deliver fluid under pressure by for example elastomeric pressure pumps. Furthermore, the flow controllers can be inserted virtually anywhere in the length of the supply tubes associated with the administration set. It is optional whether a filter is used and where in the administration set the filter would be located. Preferably the filter is located in the flow controller however, it is quite feasible to locate the filter above the flow controller. Where fluid under pressure is utilised in an administration set, ideally the pressure would operate at approximately 10 psi but could be anywhere from 1 psi to 20 psi. As indicated, the use of filters is optional however, when a filter is used in a pressurised system, the reducing effect that the filter has on the pressure must be considered in pressure selection.

According to prior art methodology, flow restriction had previously been achieved according to one embodiment by use of a small bore glass tube. It is considered that the present invention can be used as a substitute for and improvement on this method. The flow controller of the present invention in all of its embodiments is useful in any application where a restriction of flow is required in an infusion system, either operated by gravity or under pressure generated by elastomeric or other conventional means.

It will be recognised by persons skilled in the art that numerous variations and modifications can be made to the present invention without departing from the overall spirit and scope of the invention as broadly described herein.

We claim:

1. An in line fluid flow controller for use with a fluid administration set for infusion of fluid into the body of a patient, the administration set comprising means for connecting the administration set to a reservoir of fluid, said connecting means being connected to a supply line having the flow controller therein, said fluid flow controller comprising:

a housing having a chamber therein, an inlet to and an outlet from said chamber, said housing having therein a flow restrictor plate having planar opposed surfaces and an orifice or orifices extending through the plate and terminating at said planar surfaces configured to control the rate of fluid flow therethrough and into the body of a patient such that the fluid is infused into a patient at a predetermined constant flow rate or at a flow rate within predetermined limits, said housing comprising components forming said chamber and securing said restrictor plate within the housing.

2. An in line fluid flow controller for use with administration sets for infusing fluids into the body of a patient, said fluid flow controller comprising a housing having an inlet and outlet and a chamber therein having a restrictor plate, said plate having an orifice or orifices therein to control the rate of fluid flow therethrough so that fluid is infused at a predetermined rate, said housing comprising a resiliently deformable but elastic material which enables the priming of a fluid supply line or urging of fluid along said line, or urging air from said line, said housing comprising separable components for enabling insertion of said restrictor plate within the housing, said components forming said chamber and securing said restrictor plate when brought in apposition, such that a barrier is presented substantially normally to the axis of the fluid flow from said inlet to said outlet.

3. An in line fluid flow controller for use with a fluid administration set for infusion of fluid into the body of a patient, the administration set comprising means for connecting the administration set to a reservoir of fluid, said connecting means being connected to a supply line having the flow controller therein, said fluid flow controller comprising:

a housing having a chamber therein, an inlet to and an outlet from said chamber, said housing having therein a flow restrictor plate which includes an orifice or orifices configured control the rate of fluid flow therethrough and into the body of a patient such that the fluid is infused into a patient at a predetermined constant flow rate or at a flow rate within predetermined limits, said housing comprising separable components for enabling insertion of said restrictor plate within the housing, said housing being adapted for detachable or fixed attachment to the supply line of the administration set, and said housing being resiliently deformable to enable evacuation of or priming of the supply line of the administration set.

4. An in line fluid flow controller according to claim 3 wherein the controller is adapted to allow a fixed single flow rate through the restrictor.

5. An in line fluid flow controller according to claim 1 wherein said plate has one orifice therein.

6. An in line fluid flow controller according to claim 2 wherein the restrictor plate has one orifice for the passage of fluid.

7. A fluid flow controller according to claim 1 wherein the plate has more than one orifice with individual constant flows passing therethrough according to selection by a flow rate selection means.

8. An in line fluid flow controller according to claim 7 wherein the restrictor plate is substantially rectangular and has a plurality of spaced apart holes which are in alignment with the longitudinal axis of the said plate.

9. An in line flow controller according to claim 7 wherein the restrictor plate is substantially circular and has one or a plurality of orifices each radially disposed at predetermined points around the plate.

10. An in line fluid flow controller according to claim 9 wherein the said holes are of like or different diameter and are spaced at like or different intervals, 11. An in line fluid flow controller according to claim 10 wherein the restrictor plate is adapted with ribs or the like acting as crush seals between the holes to ensure that a predetermined flow rate from each hole is maintained until said flow rate selection means mixes the flows downstream of said hole or holes.

12. An in line fluid flow controller according to claim 11 wherein the said flow rate selection means comprises a moveable member with at least one through passage adapted to selectively locate so that the said passage and at least one of the holes in said restrictor plate are in alignment so as to allow fluid to exit said housing according to a predetermined flow rate dictated by said hole.

13. An in line fluid flow controller according to claim 12 wherein the said moveable member is rotatable such that selection of the flow rate is made by the degree of arcuate displacement of the rotatable member, 14. An in line fluid flow controller according to claim 13 wherein the rotatable member has in addition to said at least one through passage an associated groove which also allows passage of fluid from the particular restrictor plate which is aligned with said through passage to the outlet of said housing according to the flow rate selected.

15. An in line fluid flow controller according to claim 14 wherein the selection means enables selection of any combination of flow rates available from the restrictor plate.

16. An in line fluid flow controller according to claim 15 wherein there are five holes in the restrictor plate sized to allow selectively flow rates of 0.5 liters per day, 0.5 liters day, 1 liters per day, 2 liters per day and 3 liters per day.

17. An in line fluid flow controller according to claim 1 wherein the chamber within said housing acts as a priming chamber or fluid evacuation chamber to assist passage of fluid along or to evacuate the supply line of said administration set.

18. An in line flow controller according to claim 17 wherein the longitudinal axis of the housing is in alignment with the longitudinal axis of said supply line.

19. An in line flow controller according to claim 17 wherein the priming chamber is eccentric to the longitudinal axis of the supply line.

20. An in line flow controller according to claim 1 wherein the housing has located therein a fixed or detachable hydrophyllic filter located upstream of said restrictor plate.

21. An in line flow controller according to claim 17 wherein the flow controller is located at or near the patient end of the administration set.

22. An in line flow controller according to claim 21 wherein the restrictor hole sizes fall within the range of 5 μ to 100 μ.

23. An in line flow controller according to claim 22 wherein the flow controller is inserted into a pressure driven or gravity feed administration set.

24. An in line flow controller according to claim 23 wherein the fluid of the administration set is pressurised by an elastomeric pump prior to passing through said flow controller.

25. An in line flow controller according to claim 1 wherein the administration set is fitted with multiple flow controllers in series or parallel configuration.

26. An in line fluid flow controller as claimed in claim 1 wherein each said orifice is within the range of 5 microns to 100 microns.

27. An in line fluid flow controller as claimed in claim 1 wherein each said orifice is within the range of 50 microns to 100 microns.

* * * * *